United States Patent [19]

Geissler

[11] 4,175,099

[45] Nov. 20, 1979

[54] SEPARATION AND RECOVERY OF ETHYLBENZENE FROM $C_8$ AROMATIC MIXTURES USING RUBIDIUM-X SIEVES

[75] Inventor: Paul R. Geissler, Baton Rouge, La.

[73] Assignee: Exxon Research & Engineering Co., Florham Park, N.J.

[21] Appl. No.: 556,434

[22] Filed: Mar. 7, 1975

[51] Int. Cl.$^2$ ................................................ C07C 7/13
[52] U.S. Cl. ................................. 585/831; 208/310 Z
[58] Field of Search ............. 260/674 SA; 208/310 Z

[56] References Cited

U.S. PATENT DOCUMENTS

| | | | |
|---|---|---|---|
| 2,882,244 | 4/1959 | Milton | 252/455 |
| 3,626,020 | 3/1969 | Neuzil | 260/674 |
| 3,734,974 | 5/1973 | Neuzil | 260/674 |
| 3,943,182 | 3/1976 | Neuzil et al. | 260/674 SA |

*Primary Examiner*—Delbert E. Gantz
*Assistant Examiner*—C. E. Spresser
*Attorney, Agent, or Firm*—H. Einhorn; J. E. Callaghan

[57] ABSTRACT

A new composition of matter, a method for the preparation of a rubidium exchanged Type X structured zeolite and a separation process employing the same. The zeolite adsorbent is prepared by a procedure employing the aqueous ion exchange step and a final activation step including contacting a sodium-X zeolite with a rubidium salt in aqueous solution. The process involves the selective separation of ethylbenzene from a $C_8$ aromatic isomer mixture containing ethylbenzene and employs the use of the rubidium exchanged type X structured zeolite in an adsorption separation process.

10 Claims, No Drawings

SEPARATION AND RECOVERY OF ETHYLBENZENE FROM C₈ AROMATIC MIXTURES USING RUBIDIUM-X SIEVES

BACKGROUND OF THE INVENTION

This invention relates to a new composition of matter, the production of a zeolite adsorbent and a separation process employing same. More specifically, this invention concerns the production of a zeolite adsorbent, which preferentially adsorbs ethylbenzene from ortho-, meta- and paraxylene C₈ aromatic mixtures. The invention, therefore, also relates to a hydrocarbon separation process employing the specifically prepared sieves to effectively separate ethylbenzene from C₈ aromatic isomer mixtures of ortho-, meta-, and paraxylene.

It is well known in the separation art that certain molecular sieve adsorbents can be employed to separate paraxylene from C₈ aromatic isomer mixtures, containing ethylbenzene. The adsorbents generally employed are those as found adequately described in several patented inventions in which paraxylene is separated and recovered from C₈ aromatic isomer streams. It is also known and adequately described in U.S. Pat. No. 3,761,533 and U.S. Pat. No. 3,201,491 that in adsorption separation processes of liquid feed mixtures a technique of employing a moving bed type adsorption process wherein said moving bed comprises adsorbent particles which are countercurrently contacted with streams of liquid feedstock and desorbent, results in a high degree of purity for the adsorbed component recovered as product. This process and the so-called "simulated countercurrent flow system" wherein the solid desorbent particles are stationary have been proposed and disclosed in the above-referred to patents.

Other processes, such as commercial elution chromatography, have also been proposed for the separation of components from fluid mixtures. In these processes, the selective retardation of one or more of the components of the fluid mixture as the fluid uniformly moves through a column containing a stationary adsorbent; the retarding resulting from the distribution of the components of the mixture between the adsorbent and the bulk fluid as the fluid moves past the stationary phase. The latter process is commonly called "elution chromatography" and the separation of C₈ aromatic isomers will be operated in such a way as to pass the feed stream over an adsorbent, i.e., molecular sieve that preferentially adsorbs the paraxylene at a rate slow enough for essentially all the paraxylene to be adsorbed rather than breaking into the raffinate stream. The sieve bed could then be washed with a desorbent to desorb nonpara materials, and finally pure para could be desorbed from the sieve bed with a liquid material, i.e., desorbent, which can thereafter be easily separated from the para by distillation.

The prior art in general has not recognized the effects of rubidium ions co-exchanged with sodium ions of Type X zeolites. It has been found that the rubidium exchanged Type X zeolites generally cause the selective retention of ethylbenzene from the C₈ aromatic isomer mixture rather than the selective retention of paraxylene; hence, the use of said sieves provide a means whereby ethylbenzene may be efficiently separated and recovered from said feedstream.

SUMMARY OF THE INVENTION

In accordance with the present invention, a method for the manufacture of crystalline aluminosilicate zeolite adsorbents, i.e., sieves which, when used in a separation process would selectively separate ethylbenzene from a C₈ isomer mixture containing ethylbenzene and paraxylene. It is, therefore, an object of the present invention to provide such a method for manufacturing such sieves. It is another object of the invention to provide a process for the separation of ethylbenzene from C₈ aromatic isomer feedstreams containing ethylbenzene which process employs the specifically prepared rubidium exchanged zeolite to effectively retain a high concentration of ethylbenzene within the zeolite while effectively excluding the other components of the C₈ aromatic isomer feedstreams.

It is yet another object of the present invention to provide a composition of matter comprising rubidium in a crystalline aluminosilicate.

In accordance with the objects of the present invention, both the natural and synthetic varieties of sodium Type X structured crystalline aluminosilicates may be used as starting materials in the present invention.

Crystalline aluminosilicates are essentially cage structured material in which the alumina and silica tetrahedra are intimately connected with each other in an open three-dimensional crystalline network. The tetrahedra are cross-linked by the sharing of atoms of oxygen. The spaces between the tetrahedra are occupied by water molecules prior to dehydration. Subsequent partial or total dehydration of the zeolite results in a crystal structure interlaced with the channels of molecular dimensions. Thus, the crystalline aluminosilicates are often referred to as molecular sieves. In the hydrated form, crystalline aluminosilicates, i.e., zeolites may be represented by the general formula represented in the equation 1 below:

$$M_{2/n}O:Al_2O_3:wSiO_2:yH_2O \qquad (1)$$

wherein M is a cation which balances the electrovalence of the tetrahedra, n represents the valence of the cation, w represents the moles of SiO₂, and y the moles of water. The Type X zeolite may be represented in terms of the mole ratios of oxides for the sodium form as represented in equation 2 below:

$$0.9\pm0.2Na_2O:Al_2O_3:2.5\pm0.5SiO_2:YH_2O \qquad (2)$$

where Y may be any value up to about 8.

When the sodium form of a Type X zeolite is ion exchanged with rubidium, a portion or all of the sodium present within the zeolite structure may be replaced by the rubidium ions. The rubidium exchanged Type X structured zeolites as used in the specification shall generally encompass those zeolites which have been produced according to one embodiment of this invention and which may have essentially all of the sodium present within the zeolite originally replaced by rubidium cations to those zeolites which had only a portion of the sodium replaced by rubidium cations.

In separating the ethylbenzene from the C₈ aromatic isomer mixture containing orthoxylene, metaxylene and paraxylene, the feed stream is contacted with the bed of the rubidium exchanged sodium Type X structured zeolite, the ethylbenzene is preferentially adsorbed by the sieve while the unadsorbed raffinate mixture which comprises a portion or all of the ortho-, meta- and paraxylene components are removed from the interstitial void spaces between the adsorbent particles and the surface of the solid adsorbent. The adsorbent is then contacted with the desorbent material capable of displacing the adsorbed ethylbenzene from the adsorbent.

The adsorbent can be utilized in an elution chromatography process by having it as a single bed in a chamber through which the feedstream is allowed to flow, followed by passing over the bed a desorbent material to selectively desorb the ethylbenzene. Additionally, swing bed operational techniques where a series of adsorbent chambers are available for simulated moving bed countercurrent operations similar to those generally described in the pattern of operations as disclosed in the above patents can be used.

In the latter method of operation, the selection of a suitable desorbent requires that it be capable of readily displacing ethylbenzene from the adsorbent and, also, be capable of separation from ethylbenzene by distillation means or other separation means.

Feedstocks that may be employed will comprise $C_8$ aromatic isomer mixtures containing ethylbenzene in admixture with at least one other $C_8$ aromatic component such as orthoxylene, metaxylene and/or paraxylene.

The desorbent to be employed in the present invention can be any material satisfying the above criteria and also is not too strongly adsorbed by the sorbents so that it does not desorb ethylbenzene simultaneously with the other $C_8$ aromatic isomers. Preferably its strength of adsorption is between that of ethylbenzene and the least strongly adsorbed $C_8$ aromatic isomer present in the feed mixture.

The desorbent to be employed may be used alone or in combination with a carrier fluid or diluent such as normal paraffins, having from 10 to 20 carbon atoms, preferably from 11 to 18 carbon atoms are useful as diluents. Also useful are naphthenes which are saturated cyclic hydrocarbons, with or without alkyl substituents and which have from 6 to 20 carbon atoms, preferably from 11 to 18 carbon atoms. In this specification, carrier fluid or diluent is taken to mean liquid materials which are not significantly adsorbed by the adsorbent in the presence of feed mixture components. Desorbent or eluent is a term to describe liquid materials which are adsorbed by the substrate and compete for adsorption sites with the feed components.

When the desorbent is employed in combination with an inert diluent, such as described above, the latter usually is present in amounts of from 10 to 85 wt. %, preferably from 25 to 75 wt. %.

Process operating conditions include adsorption temperatures of from 25° to about 150° C. with desorption cycle temperatures included within the same general limits, preferably desorption and adsorption cycle temperatures are the same. The pressures which may be used are not critical and can vary from below atmospheric to many atmospheres and preferably for ease of operations below about 100 psig. The pressures at which adsorption and desorption operations are effected are preferably substantially the same.

When carrying out the present invention as a liquid elution chromatographic process, the process comprises steps such as contacting the feed mixture with the rubidium-exchanged sodium Type X sieve under conditions to effect the preferential adsorption of ethylbenzene; contacting the bed of rubidium exchanged sodium Type X zeolite containing the selectively adsorbed ethylbenzene with a carrier-eluent mixture to thereby effect the desorption of desorbed components from the bed material; recovering from the bed containing said rubidium exchanged sodium Type X sieve a stream or streams containing ethylbenzene and metaxylene, orthoxylene and/or paraxylene and mixtures thereof, and ultimately recovering ethylbenzene as pure product stream. The chromatographic process may also be modified as described in U.S. Pat. No. 3,835,043 whereby a gradient elution technique is utilized to increase the efficiency of ethylbenzene recovery. The operation of this invention in that manner utilizes the procedure as described in the above-referred to patent which is hereby incorporated by reference.

Additionally, the process may also be conducted as a simulated moving bed process in which a liquid stream containing the $C_8$ aromatic feedstream flows through serially and circularly interconnected desorption, rectification and sorption zones. In such a process, the flow of liquid stream is interrupted between both the desorption and rectification zones and a first portion of effluent from the desorption zone, a portion being rich in sorbent is directly circulated and the second portion of same comprising sorbate of high purity, i.e., ethylbenzene and desorbent is fed to a distillation apparatus from which one portion of the sorbate-distillate is circulated as a reflux to the rectification zone to maximize the sorbate product purity at reduced costs and the other portion is recovered as product. The operation of the present invention utilizing the novel rubidium exchanged sodium Type X zeolites in accordance with the simulated moving bed process employs all of the techniques and improvements as adequately described in copending applications U.S. patent application Ser. No. 556,431, filed Mar. 7, 1975 and U.S. Ser. No. 457,056, filed Apr. 1, 1974.

In testing the rubidium exchanged sodium Type X zeolite for its capacity to selectively adsorb ethylbenzene from $C_8$ aromatic isomer mixtures the following apparatus and technique was employed. The definition of alpha relative to paraxylene is as follows:

$$\text{Alpha (Equil.)} = \frac{\left.\frac{\text{Mole fraction para}}{\text{Mole fraction other } C_8}\right\} \text{Adsorbed phase}}{\left.\frac{\text{Mole fraction para}}{\text{Mole fraction other } C_8}\right\} \text{Feed}}$$

As the expression denotes the alpha values measured are actually equilibrium alpha values. Experimentally, they are obtained by passing a feed mixture containing paraxylene, metaxylene, orthoxylene and ethylbenzene over a column of freshly-calcined adsorbent until effluent composition matched that of the feed, i.e., until the adsorbed and external phases were at equilibrium. If operating liquid phase, excess feed was then swept from the column with nitrogen gas. The adsorbed phase was then desorbed with an appropriate agent, usually methyl alcohol. The feed and desorbate were separately analyzed by vapor phase chromatography.

In accordance with the present invention, the operation of the above-described processes with the novel rubidium exchanged sodium Type X sieves provides a method whereby ethylbenzene may be efficiently separated and recovered from $C_8$ aromatic isomer feedstreams.

Ethylbenzene so recovered is a salable chemical raw material for use in manufacture of styrene and for other purposes. The raffinate stream from which the ethylbenzene has been removed is particularly well suited for processing to remove paraxylene, another desirable product, and for treatment by any one of several well known xylene isomerization processes to increase the amount of paraxylene or paraxylene and orthoxylene, present. By removing the ethylbenzene, both the paraxylene removal step and the isomerization step will be made more efficient and their cost thereby reduced.

The method of which the rubidium exchanged sieves are prepared is as follows: a sodium Type X zeolite is first contacted with an aqueous solution containing rubidium cations. The aqueous solution can comprise any rubidium salt which is reasonably soluble in water such as rubidium chloride. The exchange conditions can include temperatures from about 50° C. to about 150° C. for a period of time sufficient to exchange from about 10% to essentially all of the sodium present in the sodium Type X zeolite. After the aqueous ion exchange has proceeded to the degree required, the sieve is then washed free of excess chloride ions and dehydrated at conditions including temperatures from about 100° C. to about 600° C. depending on whether total or partial dehydration of the sieve is required. It is preferred to substantially dehydrate the zeolite without rendering its crystalline structure deformed, because it is known that in most adsorption-separation processes, generally the greater the dehydration of the adsorbent, the greater the capacity of the adsorbent, for the particular species which is to be adsorbed. Consequently, total or partial dehydration renders more free volume within the zeolite which a particular hydrocarbon such as ethylbenzene sought to be separated can occupy, thereby increasing the overall capacity of the zeolite. After the preferred degree of dehydration has been accomplished, the zeolite is cooled and thereafter compacted to the desired particle size. Rubidium salts which may be employed in the exchange procedure may include rubidium chloride, rubidium acetate, rubidium bromide, rubidium chromate, rubidium iodide, rubidium nitrate, rubidium sulfate and the like.

While this invention consists of the use of novel rubidium exchanged sodium Type X zeolites and various separation processes, no limitation on the operation of these processes is intended to limit the scope of the present invention. The processes which may employ the novel sieve composition include the above-described elution chromatography and simulated moving bed processes with all of their currently described improvements.

DESCRIPTION OF THE PREFERRED EMBODIMENTS
EXAMPLES 1 through 12

Several sieves containing different cations were prepared and tested for separation alpha values by the above method. The resulting alpha values are given in Table 1.

| Example # | Wt. % Metals (On Dry. Sieve Basis) | | Sieve Type | Alpha (Paraxylene/Ethylbenzene) | $\left[\frac{Paraxylene}{Metaxylene}\right]$ |
|---|---|---|---|---|---|
| 1 | 12.7% Na | | X | 1.3 | 1.1 |
| 2 | 6.7% Na | 1.05% Rb | X | 0.76 | 1.6 |
| 3 | 0.4% Na | 31.5% Ba | X | 0.98 | 1.8 |
| 4 | 4.45% Na | 10.26% K | Y | 2.9 | 5.0 |
| 5 | 1.61% Na | 2.08% K 17.2% Ba | Y | 2.5 | 2.0 |
| 6 | 3.96% Na | 4.45% Li | X | 1.2 | 1.0 |
| 7 | 0.16% Na | 9.95% Rb | Mordenite | 1.1 | 1.0 |
| 8 | 0.18% Na | 8.89% K | Mordenite | 1.1 | 1.4 |
| 9 | 0.90% Na | 12.72% Ba | Mordenite | 1.2 | 0.9 |
| 10 | 4.8% Na | 2.03% Mg | Y | 1.4 | 0.9 |
| 11 | 0.8% Na | 32.3% Mg | Y | 1.2 | 1.0 |
| 12 | 2.5% Na | 5.95% La | Y | 1.6 | 1.0 |

The results obtained in Examples 1 through 12 show that RbX is unique in that it is the only sieve of the group tested that more strongly adsorbs ethylbenzene relative to all of the remaining xylene isomers.

What is claimed is:

1. In a process for separating ethylbenzene from a mixture of $C_8$ aromatic isomers wherein said mixture is contacted with an adsorbent which selectively adsorbs ethylbenzene under adsorbtion conditions, the improvement which comprises employing as said adsorbent an X-structured zeolite containing exchangeable cationic sites, said cations consisting essentially of rubidium and sodium and wherein said rubidium has been exchanged for at least about 10 percent of the exchangeable sodium cations.

2. The process of claim 1 further characterized in that the weight ratio of said rubidium to said sodium in said adsorbent is about 0.15:1.

3. The process of claim 1 wherein said mixture of $C_8$ aromatic isomers comprises ethylbenzene and paraxylene.

4. The process of claim 3 wherein said mixture of $C_8$ aromatic isomers comprises ethylbenzene, paraxylene, orthoxylene and metaxylene.

5. A process for separating ethylbenzene from a feed mixture containing ethylbenzene and at least one xylene isomer which comprises contacting said mixture with an adsorbent comprising X-structured zeolite containing exchangeable cationic sites and having cations consisting of sodium and rubidium and wherein said rubidium has been exchanged for at least about 10 percent of the exchangeable sodium cations said contacting being at ethylbenzene adsorption conditions including a temperature from about 25° to about 150° C. and a pressure of from about atmospheric to about 100 psig., and removing adsorbed ethylbenzene from the adsorbent.

6. The process of claim 5 further characterized in that the weight ratio of said rubidium to said sodium in said adsorbent is about 0.15:1.

7. The process of claim 5 further characterized in that said xylene isomer is para-xylene.

8. The process of claim 5 further characterized in that said xylene isomer is ortho-xylene.

9. The process of claim 5 further characterized in that said xylene isomer is meta-xylene.

10. The process of claim 5 further characterized in that said feed mixture comprises ethylbenzene, para-xylene and one other xylene isomer.

* * * * *